(12) United States Patent  
Ganter

(10) Patent No.: US 7,708,757 B2
(45) Date of Patent: May 4, 2010

(54) MEDICAL FORCEPS

(75) Inventor: Hans Ganter, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 576 days.

(21) Appl. No.: 11/210,617

(22) Filed: Aug. 24, 2005

(65) Prior Publication Data
US 2006/0047304 A1 Mar. 2, 2006

(30) Foreign Application Priority Data
Aug. 24, 2004 (DE) .................. 10 2004 041 515

(51) Int. Cl.
A61B 17/26 (2006.01)
(52) U.S. Cl. ...................... 606/205; 606/208
(58) Field of Classification Search .............. 606/170, 606/205–209, 139, 142, 174; 227/19, 27; 81/91.1, 124.5
See application file for complete search history.

(56) References Cited

U.S. PATENT DOCUMENTS

| 2,305,156 | A |   | 12/1942 | Grubel | 403/114 |
| 5,147,357 | A | * | 9/1992 | Rose et al. | 606/49 |
| 5,368,606 | A | * | 11/1994 | Marlow et al. | 606/170 |
| 5,490,819 | A | * | 2/1996 | Nicholas et al. | 600/201 |
| 5,618,303 | A | * | 4/1997 | Marlow et al. | 606/205 |
| 5,673,841 | A |   | 10/1997 | Schulze et al. | 227/175.1 |
| 5,810,879 | A | * | 9/1998 | de Guillebon | 606/205 |
| 6,036,667 | A | * | 3/2000 | Manna et al. | 604/22 |
| 6,077,290 | A | * | 6/2000 | Marini | 606/205 |
| 6,398,741 | B2 | * | 6/2002 | Niizeki et al. | 600/566 |
| 2002/0165577 | A1 | * | 11/2002 | Witt et al. | 606/205 |
| 2004/0093019 | A1 | * | 5/2004 | Kothe | 606/205 |

(Continued)

FOREIGN PATENT DOCUMENTS

DE 1 715 992 2/1956

(Continued)

OTHER PUBLICATIONS

European Search Report; Feb. 6, 2006; 3 pages.

(Continued)

Primary Examiner—Tan-Uyen (Jackie) T. Ho
Assistant Examiner—Mark Mashack
(74) Attorney, Agent, or Firm—St. Onge Steward Johnston & Reens LLC

(57) ABSTRACT

A medical forceps has a shaft, a handle at the proximal end of the shaft, which handle has at least one movable grip part which is pivotable about a pivot axis, at least one movable tool at the distal end of the shaft, and a force transmission element, which runs in the direction of the longitudinal axis of the shaft and is axially movable and with one end is in operative connection with the at least one movable tool and with the other end is in operative connection with the at least one movable grip part. The force transmission element is connected to a slide which is guided linearly with an exact fit in a sliding bearing and is axially movable in the direction of the force transmission element, the slide being connected to the movable grip part by means of an articulated lever, which is articulated with one end on the slide and with another end on the movable grip part.

10 Claims, 4 Drawing Sheets

U.S. PATENT DOCUMENTS

2004/0167569 A1* 8/2004 Dicesare et al. ............. 606/208
2004/0220601 A1* 11/2004 Lang et al. ................... 606/167

FOREIGN PATENT DOCUMENTS

| | | |
|---|---|---|
| DE | 1 055 751 | 4/1959 |
| DE | 1 266 446 | 4/1968 |
| DE | 1 644 763 | 4/1971 |
| DE | 32 15 949 A1 | 11/1983 |
| DE | 38 02 651 C2 | 8/1989 |
| DE | 3802651 A1 * | 8/1989 |
| DE | 8910462 | 1/1990 |
| DE | 69525602 T2 | 7/2002 |
| EP | 0 571 057 | 5/1993 |
| GB | 2 119 696 A | 11/1983 |

OTHER PUBLICATIONS

German Office Action, File Reference No. 102004041515.3-35, Nov. 12, 2008, 3 pages.

* cited by examiner

MEDICAL FORCEPS

CROSS REFERENCE TO RELATED APPLICATIONS

The present application claims priority of German patent application DE 10 2004 041 515.3 filed on Aug. 24, 2004.

BACKGROUND OF THE INVENTION

The invention generally relates to the field medical forceps.

A medical forceps is used in particular in the area of minimally invasive surgery for operations on a human or animal body. Without restricting generality, the medical forceps as provided by the present invention may be formed as grasping forceps for grasping tissue or as preparing forceps for cutting or preparing tissue.

A medical forceps known from the document DE 38 02 651 C2 has a handle which has a movable grip part and an immovable grip part. The movable grip part is fastened in a recess of an immovable housing part of the handle in such a way that it can pivot about a fixed pivot axis, which is arranged at the end of the movable grip part remote from the handle, which immovable housing part is for its part connected in one piece to the immovable grip part. The immovable grip part and the movable grip part project essentially transversely in relation to the longitudinal axis of the shaft of this forceps and form a scissors-grip-like arrangement. Running in the shaft in the direction of the longitudinal axis of the shaft is a force transmission element, which is movable axially in the direction of the longitudinal axis of the shaft. The force transmission element, which takes the form of a thin rod, serves for the force transmission from the movable grip part to the movable tool, for example a jaw part, at the distal end of the shaft. Correspondingly, the force transmission element is in operative connection with the movable tool on the one hand and the movable grip part on the other hand. With respect to the movable grip part, this operative connection is established by means of an articulated intermediate piece, which for its part is fastened pivotably about a fixed pivot axis in the recess of the housing part, and with which the force transmission element is articulated at an articulation point at a distance from the aforementioned fixed pivot axis. The articulated intermediate piece is connected in an articulated manner to the movable grip part by means of a pin, which engages in a slot which is arranged on the movable grip part at a distance from its fixed pivot axis.

In practical use of this medical forceps, it has been found that, in spite of observance of the smallest tolerances and the most careful production, the action of the force transmission from the movable grip part to the movable tool is not free from play. This has the disadvantage that the movable tool does not exactly follow the movements of the movable grip part. A further disadvantage of this known medical forceps is that the articulation point of the axially movable force transmission element on the articulated intermediate piece undergoes a circular movement when the movable grip part is actuated, which causes an additional movement of the force transmission element transversely in relation to the longitudinal direction of the shaft. This is one reason why this type of force transmission mechanism does not operate completely free from play.

A medical forceps which is designed in a particularly simple way with regard to the force transmission mechanism from the movable grip part to the movable tool is known from the document DE 32 15 949 A1.

In the case of this known medical forceps, the movable grip part is fastened on the immovable grip part in such a way that it can pivot about a fixed pivot axis and has a continuation which, as seen from the end of the movable grip part on the handle side, protrudes beyond the pivot axis and on which the force transmission element is directly articulated. Since this continuation undergoes a circular movement when the movable grip part pivots, here too there is once again the disadvantage that the axially movable force transmission element undergoes a circular movement.

Finally, the document DE-B 1 055 751 discloses a handle for surgical instruments which has a fixed grip part and a movable grip part, which as a difference from the two aforementioned known medical forceps run essentially in axial extension of the shaft and form a gripping arrangement which resembles a forceps grip. The movable grip part is connected by a connecting pin in an articulated manner directly to a slide, which is axially movable in the longitudinal direction of the force transmission element. The slide receives the instrument attachment. As the articulated connection of the movable grip part to the immovable grip part, arranged between the two is a leaf spring, which serves as a lever arm between the immovable grip part and the fixed grip part. The direct articulation of the movable grip part on the slide has the effect that the latter likewise does not undergo a strictly linear movement, because the articulation point of the movable grip part on the slide follows an arcuate movement curve as a result of the interposing of the leaf spring. This has as a consequence the disadvantage that the travel of the slide has to be restricted to a small range, in order to limit the circular movement of the articulation point of the movable grip part on the slide to small angles. Consequently, this force transmission mechanism is also not free from play. A further disadvantage of this force transmission mechanism is that it is only suitable for grip part arrangements in which the grip parts are arranged essentially in rectilinear extension of the shaft.

SUMMARY OF THE INVENTION

The invention is based on the object of developing a medical forceps of the type mentioned at the beginning to the extent that the force transmission mechanism from the movable grip part to the movable tool is as free from play as possible.

According to an aspect of the invention, a medical forceps is provided, comprising a shaft having a distal end, a proximal end, and a longitudinal axis. A handle is arranged at the proximal end of the shaft, the handle having at least one movable grip part, which is pivotable about a pivot axis. At least one movable tool is arranged at the distal end of the shaft. A force transmission element has a first end and a second end, and runs in direction of the longitudinal axis of the shaft and is axially movable in direction of the longitudinal axis. The first end of the force transmission element is in operative connection to the at least one movable tool. A slide guided linearly with an exact fit in a sliding bearing and being axially movable in direction of the force transmission element is provided, the second end of the force transmission element being in operative connection with the slide, the slide further being connected to the movable grip part by means of an articulated lever having a first end and a second end. The first end of said articulated lever is articulated on the slide and the second end of the articulated lever is articulated on the movable grip part.

According to the invention, the force transmission mechanism from the movable grip part to the force transmission element is accordingly formed in such a way that the force transmission element, which, as already mentioned, should as far as possible undergo only an axial movement, is connected to a likewise purely axially movable slide, which is guided with an exact fit in a sliding bearing. Instead of connecting the movable grip part directly to the slide, as in the case of the handle known from the document DE-B 1 055 751, it is provided in the case of the forceps according to the invention that the slide is connected to the movable grip part by means of an articulated lever, the articulated lever being articulated with one end on the slide and with another end on the movable grip part. The articulated lever serves for balancing out the difference in level between the articulation point on the movable grip part and the articulation point on the slide. When trying out the forceps according to the invention, it has been found that the action of the force transmission mechanism is free from play.

In a preferred refinement, the handle has an immovable housing part, which has a recess which is open on one side, in which one end of the movable grip part engages and in which this end is fastened in such a way that it can pivot about the pivot axis, and the sliding bearing for the slide essentially closes the recess.

In the case of the medical forceps known from the document DE 38 02 651 C1, the articulated intermediate piece is indeed also arranged in the recess of the housing part, but in the case of this known forceps the articulated intermediate piece closes the recess only inadequately, since the articulated intermediate piece must of course undergo a movement when the movable grip part moves. By contrast, the sliding bearing of the forceps according to the invention is an immovable part and can accordingly be formed with regard to its geometry in such a way that it at least essentially closes the recess. One advantage that is achieved thereby is that fewer contaminants can penetrate into the recess of the housing part.

In a further preferred refinement, the sliding bearing is formed as a separate component.

One advantage of this measure is the simpler way in which the forceps according to the invention can be produced, because the machining of the sliding bearing can be performed separately from the machining of, for example, the aforementioned housing part.

In a further preferred refinement, the sliding bearing is adapted with regard to its shape in such a way that it finishes flush with the edge of the recess of the housing part.

Here it is of advantage that the housing part has on all sides essentially a smooth surface that is free from projections, which also significantly improves the aesthetic appearance of the forceps according to the invention.

In a further preferred refinement, the slide and/or the sliding bearing has/have a length which is greater than the maximum path of movement of the slide in the sliding bearing.

Here it is of advantage that the exact linear guidance of the slide in the sliding bearing is further improved; in particular, tilting, and consequently canting, of the slide in the sliding bearing is avoided.

In a further preferred refinement, the articulated lever is fixed in an articulated manner on the slide and the movable grip part by means of a rivet in each case.

The connection of the articulated lever by means of rivets to the slide and to the movable grip part advantageously contributes additionally to the freedom from play of the action of the force transmission mechanism.

In a further preferred refinement, the slide is arranged offset parallel with respect to the force transmission element and has a laterally projecting driver, on which the force transmission element is fixed.

This configuration is of advantage in particular if the grip arrangement of the handle of the forceps is formed in a scissors-grip-like manner. In this case, the parallel offset arrangement of the slide with respect to the force transmission element can avoid the articulated lever forming an angle with the slide that is too acute. Rather, the angle between the slide and the articulated lever can be chosen to be obtuse, for example over 130°, preferably over 150°, whereby the easy and play-free action of the mechanism is improved.

In a further preferred refinement, the articulated lever is articulated with one end between two legs of a forked portion of the movable grip part and with the other end between two legs of a forked portion of the slide.

This measure also advantageously contributes to the further improvement of the freedom from play of the action of the force transmission mechanism, because the articulated lever, for example a small plate, can be mounted between the respective legs of the forked portions in such a way that it is free from tilting.

In another preferred refinement, the handle has an immovable grip part, the movable grip part and the immovable grip part projecting essentially transversely in relation to the longitudinal axis of the shaft and together forming a scissors-grip arrangement.

As a difference from the handle known from the document DE-B 1 055 751, this grip arrangement, preferred by doctors, is only made possible by the force transmission mechanism according to the invention.

Further advantages and features emerge from the following description and the accompanying drawing.

It goes without saying that the features mentioned above and those still to be explained below can be used not only in the respectively specified combination but also in other combinations or on their own without departing from the scope of the present invention.

BRIEF DESCRIPTION OF THE DRAWINGS

An exemplary embodiment is represented in the drawing and is described in more detail with reference to the said drawing, in which.

DETAILED DESCRIPTION OF THE DRAWINGS

Figure 1:
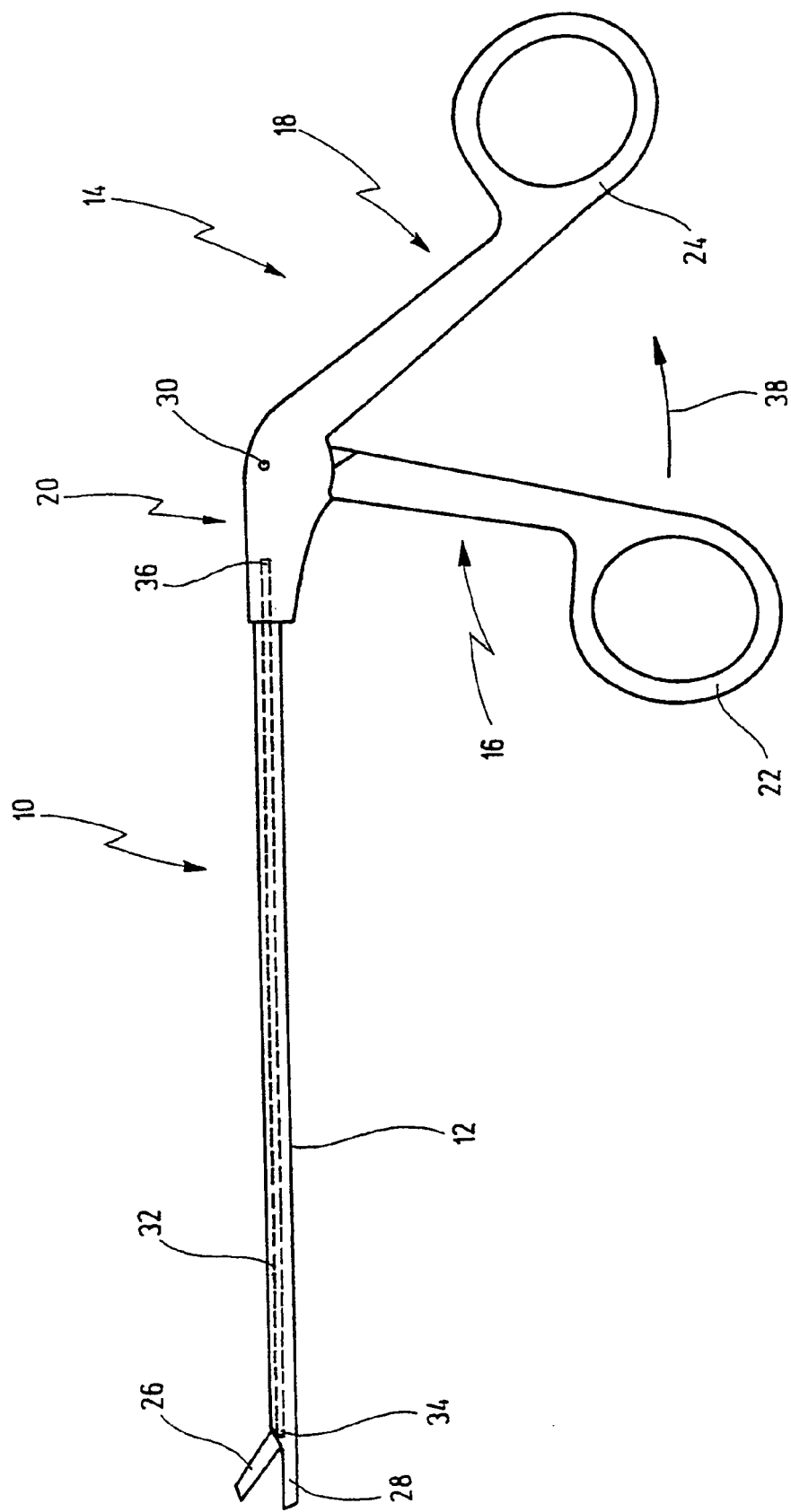
FIG. 1 shows a medical forceps in side view.

In FIG. 1, a medical forceps provided with the general reference numeral 10 is represented. The forceps 10 is used in the area of surgical operations on a human or animal body, in particular in endoscope-assisted minimally invasive surgery.

The forceps 10 has an elongated shaft 12, which has a small diameter, so that the shaft 12 can be inserted through a narrow incision into the body of a patient.

At the proximal end of the shaft 12, the forceps 10 has a handle 14. The handle 14 has a movable grip part 16 and an immovable grip part 18. Furthermore, the handle 14 has a housing part 20, which is connected to the immovable grip part 18, preferably in one piece.

The movable grip part 16 has a finger ring 22 for inserting the index finger and/or middle finger, and the immovable grip part 18 similarly has a finger ring 24 for inserting the thumb.

At the distal end of the shaft 12, the forceps 10 has a movable tool 26 and an immovable tool 28. However, like the tool 26, the tool 28 may be movable.

Depending on the intended use of the forceps 10, the tools 26 and 28 interact in a cutting or grasping manner.

The movable grip part 16 is fastened on the housing part 20 of the handle 14 in such a way that it can pivot about a fixed pivot axis 30. The pivoting of the movable grip part 16 serves for the moving of the movable tool 26. In order to transmit the force from the movable grip part 16 to the movable tool 26, there is a force transmission element 32, which is represented in FIG. 1 by interrupted lines. The force transmission element 32, for example a pulling and pushing wire or rod, runs in the direction of the longitudinal axis of the shaft 12 and is axially movable in relation to the latter. In the exemplary embodiment shown, the shaft 12 is formed as a tube, and the force transmission element 32 runs correspondingly inside the shaft 12.

Figure 2:
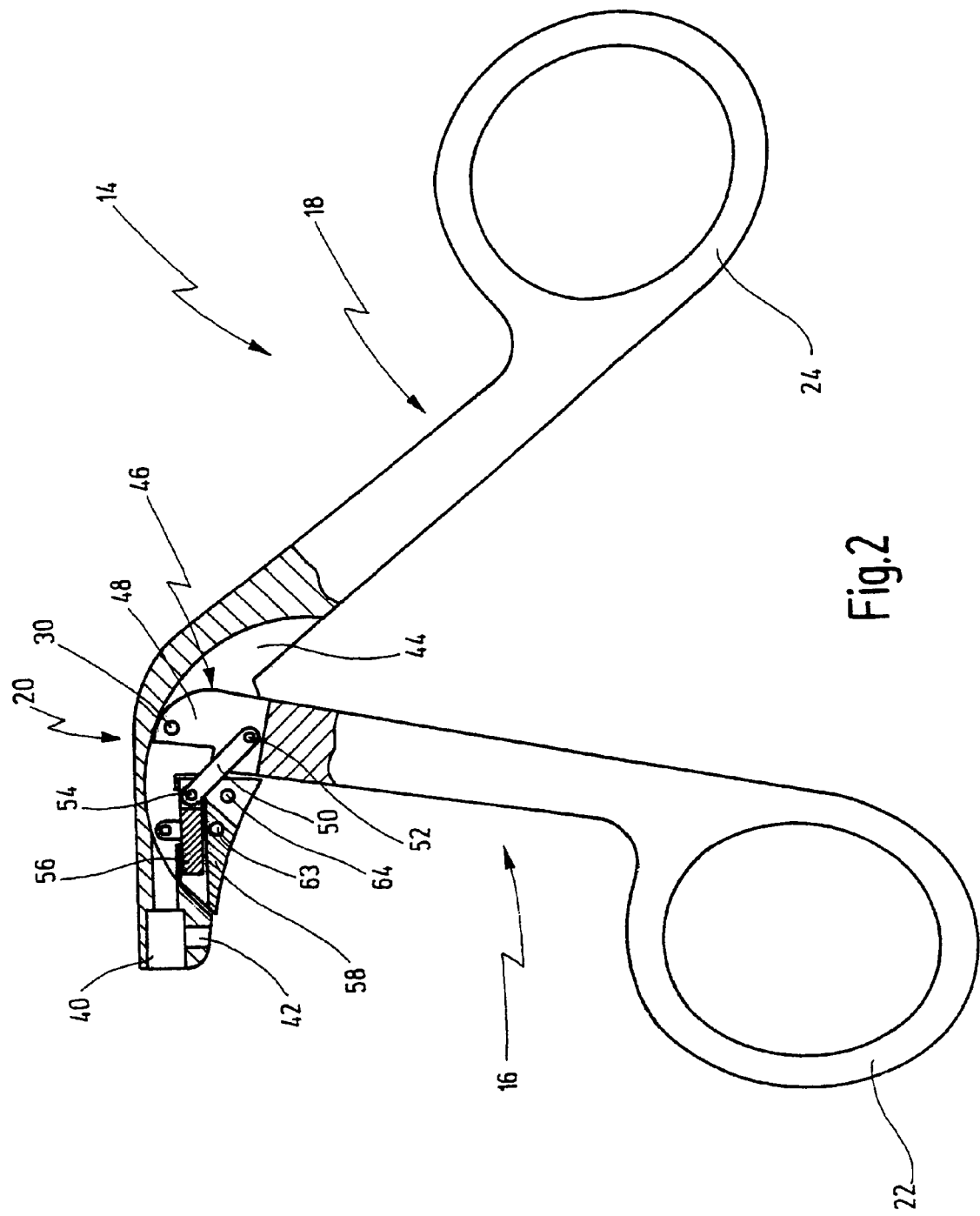
FIG. 2 shows the handle of the forceps in FIG. 1 on its own, on an enlarged scale and partly in section, in a first operating position.
Figure 3:
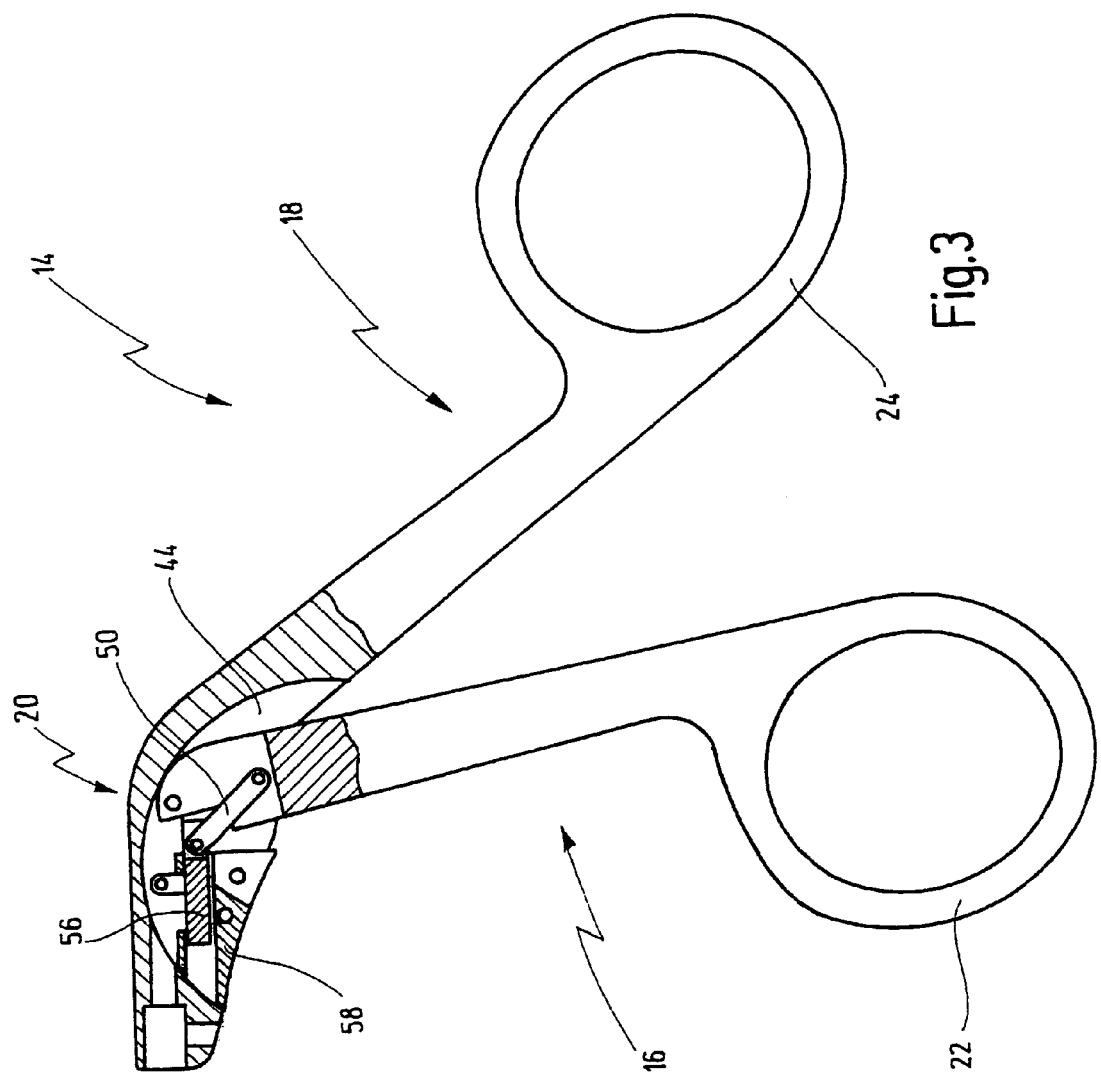
FIG. 3 shows the handle in FIG. 2 in a second operating position.
Figure 4:
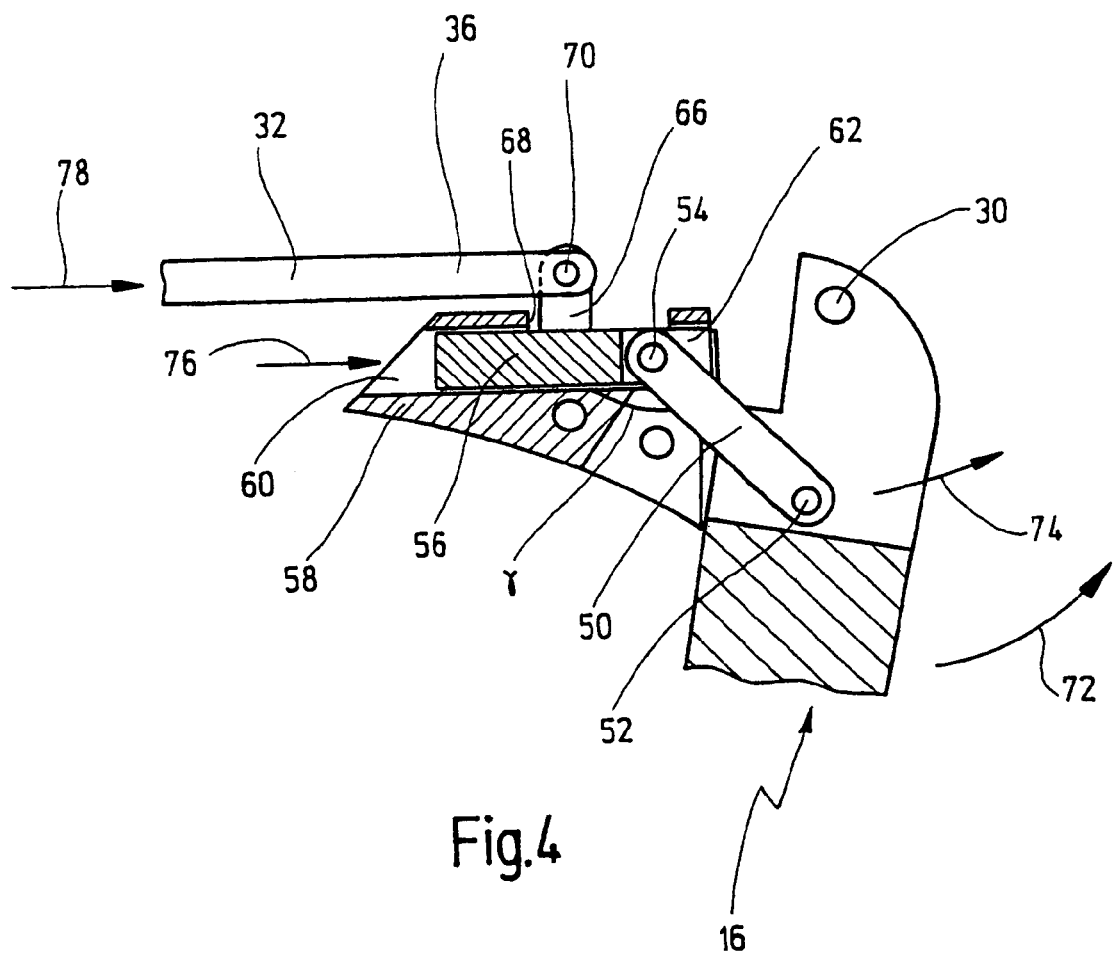
FIG. 4 shows an isolated representation of the force transmission mechanism of the handle in FIGS. 2 and 3 of the forceps in FIG. 1.

With one end, the force transmission element 32 is in operative connection with the movable tool 26, and, with another end 36, the force transmission element 32 is in operative connection with the movable grip part 16, as described in more detail hereafter with reference to FIGS. 2 to 4.

The end 34 of the force transmission element 32 is connected to the movable tool 26 for example by means of an articulated lever arrangement (not shown).

In FIG. 1, the movable tool 26 is shown in its open position, with respect to the immovable tool 28, in which the movable grip part 16 is at a maximum distance from the immovable grip part 18. By pivoting of the movable grip part 16 in the direction of an arrow 38 about the pivot axis 30 in the direction of the immovable grip part 18, the movable tool is moved by mediation of the force transmission element 32 towards the immovable tool 28 until it is in its closed position. In the closed position of the tools 26 and 28, the grip parts 16 and 18 close together, without however lying against each other, as represented in FIG. 3, which shows the position of the grip parts 16 and 18 as close together as they come.

The grip parts 16 and 18 are formed in such a way that they project from the shaft 12 essentially transversely in relation to the longitudinal axis of the shaft 12 and together form a scissors-grip arrangement.

With reference to FIGS. 2 to 4, further details are now described, in particular of the force transmission mechanism from the movable grip part 16 to the force transmission element 32.

According to FIG. 2, the housing part 20 of the handle 14 has at its distal end a bore 40 for receiving the proximal end of the shaft 12. For securely clamping the proximal end of the shaft 12 in the bore 40, a grub screw (not shown in any more detail) is screwed in via a further bore 42, which runs transversely in relation to the bore 40.

The housing part 20, which is connected in one piece to the immovable grip part 18, has a recess 44, which is open on one side and is formed in an approximately crescent-shaped manner. The recess 44 is open on one side, to be precise on its side facing the movable grip part 16.

Protruding into this recess is an end 46 of the movable grip part 16, which is remote from the handle and is fixed at the fixed pivot axis 30, which is formed for example by a pin. The end 46 of the movable grip part 16 is formed as a forked portion, of which only one leg 48 can be seen in FIG. 2.

At a distance from the pivot axis 30, an articulated lever 50 is articulated with one end at an articulation point 52 on the movable grip part 16. With respect to the pivot axis 30, the articulation point 52 lies in front of the pivot axis 30, as seen from the end on the handle side (finger ring 22).

At the articulation point 52, the articulated lever 50 is fixed on the movable grip part 16 by means of a rivet. The articulated lever 50 thereby engages in the forked portion of the movable grip part 16, of which, as already mentioned, only the leg 48 can be seen in FIG. 2.

As revealed most clearly by FIG. 4, the articulated lever 50 is articulated with its other end at an articulation point 54 on a slide 56, which is guided with an exact fit in a sliding bearing 58, the slide 56 being displaceable exclusively linearly in the direction of the force transmission element 32. The sliding bearing 58 has a corresponding exact-fit bore 60, which is, for example, an H7 bore, that is a bore produced with very small tolerances. The slide 56 is mounted in the bore 60 of the sliding bearing 58 without radial play.

At its proximal end, the slide 56 has in the region of the articulation point 54 a forked portion, of which only one leg 62 can be seen in FIG. 4.

Again with reference to FIG. 2, the sliding bearing 58, which is a separate component, is inserted in the recess 44 of the housing part 20 and immovably fixed on the housing part 20 by means of two exactly fitting pins 63 and 64.

The articulation point 54 of the articulated lever 50 on the slide 56 is likewise formed in a play-free manner by a rivet.

The sliding bearing 58 is adapted with regard to its outer contour in such a way that it essentially closes the recess 44 on the distal side of the movable grip part 16 and thereby finishes flush with the edge of the recess 44 of the housing part 20. Consequently, the upper side of the recess 44 is closed apart from small open regions, which ensure the movability of the movable grip part 16 in the recess 44.

FIG. 2 shows the slide 56 in its most distal position, which corresponds to the open position of the tools 26, 28 or the position of the movable grip part 16 at the greatest distance from the immovable grip part 18, and FIG. 3 shows the slide 56 in the most proximal position, which corresponds to the closed position of the tools 26, 28 or the position of the immovable grip part 16 with respect to the immovable grip part 18 in which they are as close together as they come.

As revealed by FIG. 4 in particular, the slide 56 is arranged offset parallel with respect to the force transmission element 32 and has a laterally projecting driver 66, which is fixedly connected to the slide 56. The driver 66 protrudes from an opening in the sliding bearing 58, the driver 66 forming in interaction with the edges of the opening 68 in the sliding bearing 58 in each case a stop for the most distal and most proximal positions of the slide 56. In this way, the slide 56 is also captively held in the sliding bearing 58.

The maximum path of movement of the slide 56 in the sliding bearing 58 is consequently determined by the axial width of the opening 68 in the sliding bearing 58 and by the axial width of the driver element 66.

The length of the slide 56 and the length of the sliding bearing 58 or the bore 60 are chosen to be greater than the maximum path of movement of the slide 56 in the sliding bearing 58.

The force transmission element 32 is fixed with its end 36 at an articulation point 70 on the driver element 66.

The articulated lever 50 forms an obtuse angle γ with the slide 56 (cf. FIG. 4), which is made possible in particular by the parallel offset arrangement between the slide 56 and the force transmission element 32.

The mode of operation of the force transmission mechanism from the movable grip part 16 to the force transmission element 32 is described below with reference to FIG. 4 in conjunction with FIGS. 2 and 3.

FIG. 4 shows the movable grip part 16 in the same position as in FIG. 2, i.e. in the open position, in which it is spread the most away from the immovable grip part 18.

If then, starting from this position, the movable grip part 16 is pivoted about the fixed pivot axis 30 according to an arrow 72, the articulation point 52 of the articulated lever 50 likewise undergoes a pivoting movement in the direction of an arrow 74. This movement has the effect that the articulated lever 50 exerts a tension on the slide 56, whereby the slide 56 is pulled back in the direction of an arrow 76. As a result of the articulation of the articulated lever 50 both on the movable grip part 16 and on the slide 56 and its exactly fitting guidance in the sliding bearing 58, essentially no transverse forces act on the slide 56, so that the latter undergoes an easy-action, purely linear movement in the bore 60 of the sliding bearing 58. By means of the driver 66, the force transmission element 32 is then likewise pulled purely axially in the proximal sense in the direction of an arrow 78 (the force transmission element 32 is not depicted in FIGS. 2 and 3).

The reverse movement of the movable grip part 16 from the closed position, represented in FIG. 3, into the open position, represented in FIG. 2, correspondingly leads to an axial movement of the force transmission element 32 in the distal sense.

What is claimed is:

1. A medical forceps, comprising
   a shaft having a distal end, a proximal end, and a longitudinal axis,
   a handle arranged at said proximal end of said shaft, said handle having at least one movable grip part, which is pivotable about a pivot axis,
   at least one movable tool arranged at said distal end of said shaft,
   a force transmission mechanism acting between said at least one movable grip part and said at least one movable tool, said force transmission mechanism acting without play and comprising:
   a force transmission element having a first end and a second end, and running in direction of said longitudinal axis of said shaft and being axially movable in direction of said longitudinal axis, said first end of said force transmission element being in operative connection to said at least one movable tool,
   a slide guided linearly with an exact fit in a sliding bearing and being axially movable in direction of said force transmission element, said second end of said force transmission element being in operative connection with said slide, said slide further being connected to said movable grip part by means of an articulated lever having a first end and a second end, said first end of said articulated lever being articulated on said slide and said second end of said articulated lever being articulated on said movable grip part,
   wherein said slide is arranged offset transverse to said longitudinal axis of said shaft in direction to said movable grip part and parallel with respect to said force transmission element, and has a laterally projecting driver, on which said second end of said force transmission element is fixed; and
   wherein said slide and a point at which said articulated lever is articulated on said slide are spaced apart from said force transmission element toward said movable grip part in direction transverse to said longitudinal axis of said shaft.

2. The forceps of claim 1, wherein said handle has an immovable housing part, which has a recess which is open on one side, in which one end of said movable grip part engages and in which said end of said movable grip part is fastened in such a way that it can pivot about said pivot axis, and wherein said sliding bearing for said slide essentially closes said recess.

3. The forceps of claim 1, wherein said sliding bearing is formed as a separate component.

4. The forceps of claim 2, wherein said sliding bearing is adapted with regard to its shape in such a way that said sliding bearing finishes flush with an edge of said recess of said housing part.

5. The forceps of claim 1, wherein said slide has a length which is greater than a maximum path of movement of said slide in said sliding bearing.

6. The forceps of claim 1, wherein said sliding bearing has a length which is greater than a maximum path of movement of said slide in said sliding bearing.

7. The forceps of claim 1, wherein said articulated lever is fixed in an articulated manner on said slide and said movable grip part by a rivet in each case.

8. The forceps of claim 1, wherein said second end of said articulated lever is articulated between two legs of a forked portion of said movable grip part.

9. The forceps of claim 1, wherein said first end of said articulated lever is articulated between two legs of a forked portion of said slide.

10. The forceps of claim 1, wherein said handle further has an immovable grip part, said movable grip part and said immovable grip part projecting essentially trans-versely in relation to said longitudinal axis of said shaft and together forming a scissors-grip arrangement.

\* \* \* \* \*